(12) United States Patent
Erdelmeier et al.

(10) Patent No.: US 7,381,429 B2
(45) Date of Patent: Jun. 3, 2008

(54) EXTRACTS FROM SOPHORA SPECIES, METHOD FOR PRODUCING THE SAME AND THEIR USE

(75) Inventors: Clemens Erdelmeier, Karlsruhe (DE); Hermann Jaggy, Karlsruhe (DE); Egon Koch, Karlsruhe (DE)

(73) Assignee: Dr. Willmar Schwabe GmbH & Co., Karlsruhe (DE)

( * ) Notice: Subject to any disclaimer, the term of this patent is extended or adjusted under 35 U.S.C. 154(b) by 274 days.

(21) Appl. No.: 10/312,613

(22) PCT Filed: Jun. 29, 2001

(86) PCT No.: PCT/DE01/02460

§ 371 (c)(1),
(2), (4) Date: May 23, 2003

(87) PCT Pub. No.: WO02/00236

PCT Pub. Date: Jan. 3, 2002

(65) Prior Publication Data

US 2003/0180394 A1 Sep. 25, 2003

(30) Foreign Application Priority Data

Jun. 29, 2000 (DE) ............................. 100 31 651

(51) Int. Cl.
*A01N 65/00* (2006.01)
(52) U.S. Cl. .................................................... 424/725
(58) Field of Classification Search ................. 424/725
See application file for complete search history.

(56) References Cited

FOREIGN PATENT DOCUMENTS

| CN | 1099259 | * | 3/1995 |
|---|---|---|---|
| CN | 1147401 | A | 4/1997 |
| CN | 1151878 | A | 6/1997 |
| CN | 1175458 | A | 3/1998 |
| CN | 1177478 | * | 4/1998 |
| EP | 0 998 924 | A | 5/2000 |
| JP | 08073364 | * | 3/1996 |
| JP | 10017460 | * | 1/1998 |
| JP | 10017461 | * | 1/1998 |
| SU | 1697819 | A1 | 12/1991 |

OTHER PUBLICATIONS

Mao Hui-Sheng Liu Hong-Yin, Li Chuan, "Modulation of the malignant phenol-type and the immunological response of tumor cells by Sophora flavescens Ait (AF-7)", vol. 23, No. 11, 1996, pp. 799-803 (English Abstract only).
Mashahiro Kitaoka, et al., prenylflavonoids: A New Class of Non-Steroidal Phytoestrogen (Part 1). Isolation of 8-Isopentenylnaringenin and an Initial Study on its Structure-Activity Relationship:, Planta Medica 64 (1998), pp. 511-515.
Masanori Kuroyanagi, et al., "Antibacterial and Antiandrogen Flavonoids from Sophora flavescens", Journal of Natural Products, 1999, vol. 62, No. 12, pp. 1595-1599 (already cited in the application itself).
Ping Xiao, et al., "(-)-14β-Hydroxymatrine, a New Lupine Alkaloid from the Roots of Sophora tonkinensis", Chem. Pharm. Bull. 44(10), pp. 1951-1953 (1996).
Yang Fuquan, et al., "Preparative separation of alkaloids from the root of Sophora flavescens Ait by pH-zone-refining counter-current chromatography", Journal of Chromatography A, 822 (1998), pp. 316-320.
Milligan et al. (1999), *J. Clin. Endocrinol. Metab.*, vol. 84, pp. 2249-2252.
Tham et al. (1998), *J. Clin. Endocrinol. Metab.*, vol. 83, pp. 2223-2235.
Kuroyanagi et al. (1999), *J. Natural Products*, vol. 62, pp. 1595-1599.
Mazur et al. (1998), *Nutritional Biochemistry*, vol. 9, pp. 193-200.
Huang, K.C. (1993), *The Pharmacology of Chinese Herbs*, CRC Press, Boca Raton, pp. 63-66.
Huang, K.C. (1993), *The Pharmacology of Chinese Herbs*, CRC Press, Boca Raton, pp. 302-303.
Tang et al. (1992), *Chinese Drugs of Plant Origin*, Springer Verlag, Berlin, pp. 931-943.
Sophorae Flavescentis Radix, "Kushen," Arzneibuch der Chinesischen Medizin (Pharmacopoeia of Chinese Medicine), Sep. 1997, pp. 1-5.
Blaszcyzk, T. (2001), *Deutsche Apoth. Zig.*, vol. 141, pp. 1687-1697.
Shi Young Ryu et al. "In Vitro Antitumor Activity of Flavonoids from Sophora Flavescens" *Phytotherapy Research*, vol. 11, pp. 51-53 (1997).
Ko, W. G., et al. "Lavandulylflavonoids: A New Class of In Vitro Apoptogenic Agents from Sophora Flavescens." Database Biosis Online, Database accession No. PREV200000462363; Toxicology in Vitro, vol. 14, No. 5, pp. 429-433 (Oct. 2000).
Patent Abstracts of Japan, Publication No. 02073079, vol. 014, No. 254 (May 13, 1990).
Patent Abstracts of Japan, Publication No. 00154118 A, (Jun. 6, 2000).
WPIDS: AN 1999-303241 [26]: "Medicine for treating Cancer-Prepared from Chinese Medicinal Materials, e.g. Oldenlandia, Aloies and Natural Indigo . . . ". Wang, C., CN 1207313 A 19990210 (199926).

* cited by examiner

*Primary Examiner*—Michael Meller
(74) *Attorney, Agent, or Firm*—McDonnell Boehnen Hulbert & Berghoff LLP

(57) ABSTRACT

The invention relates to extracts from *Sophora* species, to a method for producing the same and to their use in the prophylaxis and therapy of pathological conditions that are caused by estrogen deficiency or by other hormonal dysregulations.

4 Claims, 3 Drawing Sheets

EXTRACTS FROM SOPHORA SPECIES, METHOD FOR PRODUCING THE SAME AND THEIR USE

The present invention relates to extracts of Sophora species, methods for producing the same and their use for the prophylaxis and treatment of pathological conditions caused by oestrogen deficiency or by dysregulations of sex hormone metabolism, in particular oestrogen metabolism.

Irregular menstrual cycles appear in women from around the age of 40, marking the onset of the menopause. This phase of changes in the endocrine system, known as the climacteric, may persist for a decade or more. It results from the exhaustion of follicle growth and reduced responses to gonadotropin. As a consequence of this follicle deficit, production of oestrogen declines and eventually stops altogether. In association with this, a variety of symptoms may develop, such as hot flushes, depression, anxiety, mental confusion, insomnia etc. In addition to these, serious health problems may arise as a result of the decline in oestrogen production, such as osteoporosis, cardiac insufficiency, cerebral infarction (strokes) and cancer.

Although hormone replacement therapy with oestrogens for the relief of climacteric-related complaints is highly effective, numerous studies show that an increased risk of breast cancer and cancer of the womb, cardiovascular diseases and changes to liver metabolism can be linked to this. The risk of cancer can be reduced by administering progestines. However, the protective effect of progestines appears to fade with long-term use and it is thought that hormone replacement therapy (HRT) is linked with a 35-40% increased risk of breast cancer. Given the side effects, also distinct doubts as to the reliability of this type of treatment, the use of HRT medicine in post-menopausal women over age 40 tends to be refused. It is estimated that only around 20% of post-menopausal American women receive HRT, of whom just 40% continue with the treatment for longer than one year.

Substances that have an oestrogen-agonistic effect in humans or animals, or which interact with oestrogen, have been discovered in many plants. At least 20 different groups of substances with oestrogenic/anti-oestrogenic properties, coming from over 300 plants of more than 16 families of plants, have thus far been found. The majority of the known phyto-oestrogens belong to the isoflavone, lignane or cumestane families. Only recently, a further highly potent phyto-oestrogen has been identified —8-prenylnaringenine (S. R. Milligan et al; Journal of Clin. Endocrinol. Metab. 84, 2249- 2252 [1999]). The oestrogenic potency of 8-prenyl-naringenine in vitro was tested by stimulating alkaline phosphatase in Ishikawa-Var-I cells. In so doing, it was found that 8-prenylnaringenine was significantly more active than the phyto-oestrogens known so far, such as coumestrol, genistein or daidzein, and produced only a slightly weaker effect than 17β oestradiol.

Controlled epidemiological studies on populations in the USA, Europe, China and Japan have shown that a close negative correlation exists between the uptake of phyto-oestrogens with food and the appearance of various tumours, especially breast cancer and prostate cancer. The inhibiting effects of phyto-oestrogens on the growth of mammary and prostate tumour cells have also been confirmed in animal experiments. The preventive properties of phyto-oestrogens are obviously based on a large number of different biological properties that differentiate these substances from synthetic and natural oestrogens. Depending on the dosage and the endogenous hormone status, phyto-oestrogens also have oestrogenic or even anti-oestrogenic effects. Other biological effects include, for example, the inhibition of tyrosinkinases, DNA topoisomerases, ribosomal S6 kinase, ornithindecarboxylase, aromatase and 5α reductase. Moreover, phyto-oestrogens frequently have anti-oxidising properties and it is clear that the sum total of all these various activities plays a part in inhibiting the appearance and growth of tumours (Tham et al, Journal of Clin. Endocrin. Metab. 83, 2223-2235 [1998]).

The object underlying the present invention is to provide plant extracts that are suitable for the prophylaxis and treatment of pathological conditions that are caused by an oestrogen deficiency or by a dysregulation of sex hormone metabolism, in particular oestrogen metabolism.

A further object of the present invention is to provide a method for producing the extracts.

These objects are solved according to the invention described herein.

Several Sophora species (Fabaceae) are known from traditional Chinese medicine whose roots can be used medicinally. These are Sophora flavescens, S. subprostrata, S. alopeculoides, S. japonica, S. tonkinensis, S. tomentosa, S. moorcroftiana and S. leachiana. Of these, S. flavescens turns out to be of special significance. For this reason, it is found in the Chinese Pharmacopoeia (Sophorae flavescentis radix, "Kushen", Pharmacopoeia of Chinese Medicine 9/1997) and is traditionally used for the treatment of diarrhoea, gastro-intestinal haemorrhaging and eczema (W. Tang, G. Eisenbrand, Chinese Drugs of Plant Origin, Springer Verlag, Berlin 1992).

S. flavescens roots, as well as those of other Sophora species, contain variety of chinolizidine alkaloids as their main ingredients. The Chinese Pharmacopoeia stipulates that the total titrimetric content of alkaloids may not fall below 2%. The main alkaloids are matrine and oxymatrine.

Besides the alkaloids, a large number of flavones and related compounds and triterpensaponines were found in the roots of S. flavescens, as well as in quite a few other Sophora species.

A variety of pharmacological properties have been described for Sophora flavescens, also for individual ingredients or groups of ingredients. Alkaloids, in particular, have been thought to account for anti-arrhythmic, anti-asthmatic and anti-tussive effects, also for anti-ulcer effects (Tang and Eisenbrand, see above). Anti-neoplastic effects and immune-suppressant properties have also been observed.

M. Kuroyanagi et al, Journal of Natural Products 1999, 62 (12) 1595-1599, report on anti-bacterial and anti-androgenic flavonoids from Sophora flavescens. It was found that virtually all prenylflavone derivatives isolated from Sophora flavescens showed an anti-androgenic effect.

W. M. Mazur et al, Nutritional Biochemistry 1998, 9, 193-200, report on the quantitative determination of the isoflavones formononetin, biochanin A, daidzein, genistein and coumestrol and the lignanes secoisolariciresinol and matairesinol in leguminosae seeds, when seeds of Sophora japonica were investigated among others.

In toxicology, S. flavescens and S. japonica are classified as toxic. In particular, alkaloids of the matrine type are thought to be poisonous (T. Blaszczyk, Deutsche Apotheke Zeitung 2001, 141 [14], 1687-1696). In clinical samples, toxic effects such as severe palpitations, dyspnea and spasms were observed in the case of Sophora alkaloids. In animal studies, toxic effects could be shown for oxymatrine (K. -C. Huang, The Pharmacology of Chinese Herbs, CRC press, Boca Raton, 1993).

EP 0 998 924 A1 describes an anti-tumour agent which contains compounds obtainable from plants with a topoisomerase II-inhibiting activity. Thus, in example 8, a description of obtaining leachianol A from *Sophora* is included. In this example, a dry powder of *Sophora* was subjected to sequential extraction with acetone and methanol under reflux. The acetone extract was concentrated at reduced pressure and mixed with water. The resulting mixture is subjected to incremental distribution extraction by the use of benzene, ethylacetate and n-butanol. The ethylacetate extract is concentrated at reduced pressure and, in this way, a residue is obtained. The residue thus obtained is cleaned by silica-gel chromatography, using a benzene-acetone solvent mixture; in so doing, leachianol A is obtained. The ethylacetate extract described in example 8 differs from the extract of this invention in that extracts obtained according to the invention contain maackiain, and maackiain glucoside is greatly enriched (approx. five-fold). In both these compounds, we are dealing with ingredients that are relevant to the effectiveness of the extract according to the invention, as the inventors were able to show for the first time with the aid of an oestrogen receptor-bonding assay according to example 5. EP 0 998 924 A1 gives no suggestion of the use of extracts of *Sophora* species for the prophylaxis and treatment of pathological conditions that are caused by oestrogen deficiency or by dysregulation of sex hormone metabolism, in particular oestrogen metabolism.

Species of *Sophora* particularly favoured for the present invention are *Sophora flavescens* and *Sophora subprostrata*, for their aqueous-alcoholic root extracts were found to have surprisingly powerful oestrogenic effects in the context of this invention. It was possible to enrich these aqueous-alcoholic extracts by further separation and purification. It turned out that pharmacological effects observed were caused by the interaction of the isoflavones present in the extracts: genistein and daidzein, flavones such as 8-prenylnaringenine, kushenol X, 8-prenylkaempferol, leachianon G and kushenol E, chalcones and pterocarpanes such as maackiain and maackiain glucoside, as well as other unidentified flavonide-like compounds. In this connection, the chalcone newly discovered by the inventors: 2, 4, 4', 6' tetrahydroxy- 3'-lavandulyl- 2'-methoxychalcone of the formula below should also be mentioned.

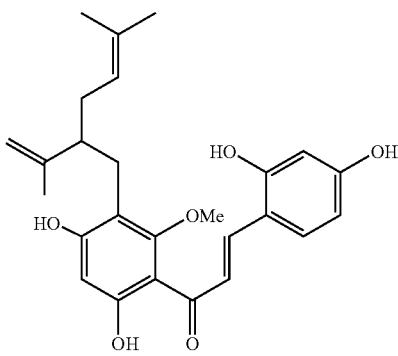

Figure 1:
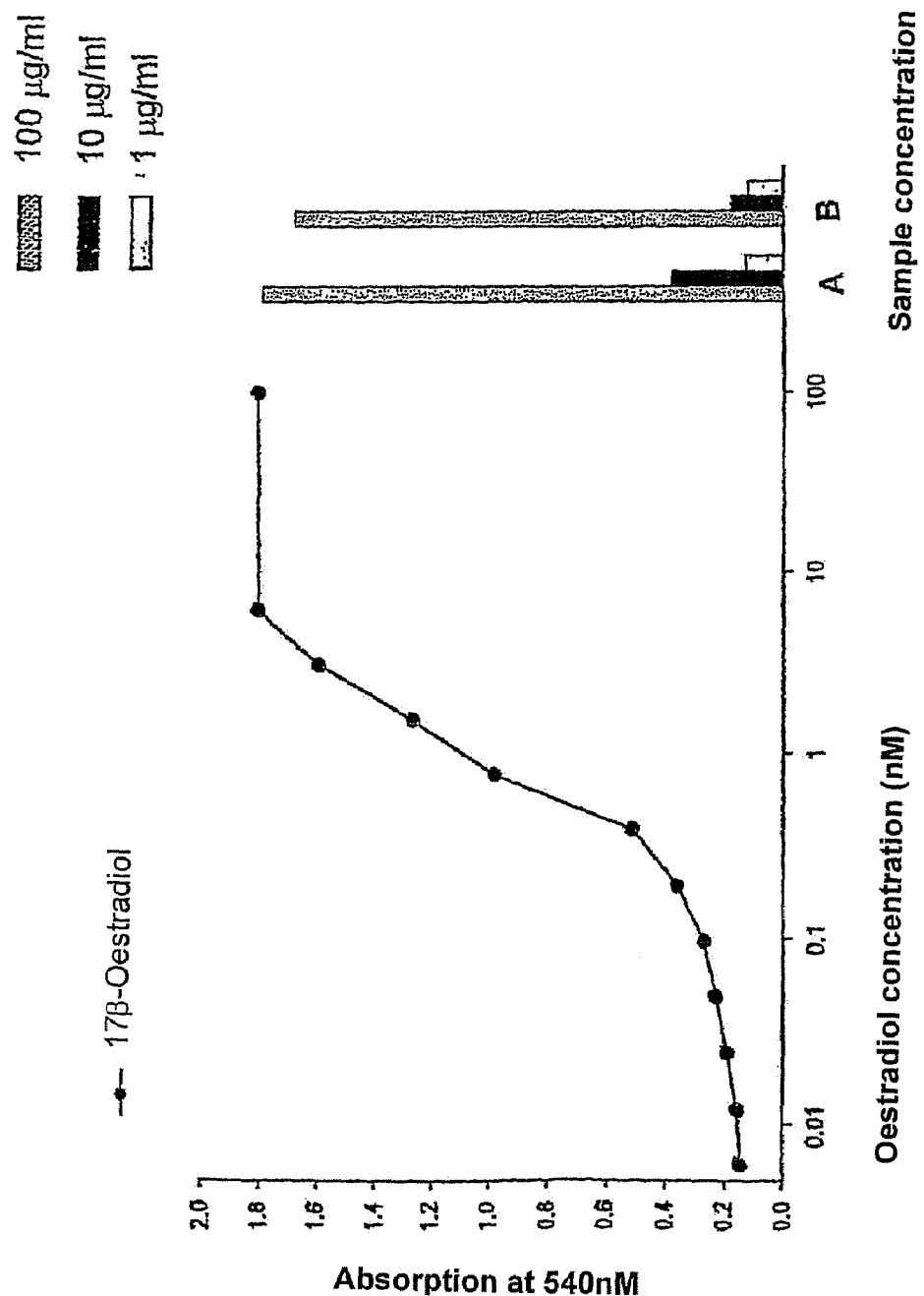
FIG. 1 illustrates the oestrogenic activity of 70% [v/v] (62% [w/w]) ethanol extracts (according to examples 1a) and 2a)) from *Sophora flavescens* and *Sophora subprostrata* in a yeast assay, compared with 17β oestradiol.

Similar extracts can generally be obtained by extraction with a solvent of medium polarity, chosen from the group consisting of aqueous alcohols, aqueous ketones and esters, including aqueous or water-saturated esters, draining off the solvent and subsequent fluid-fluid distribution between an organic solvent and water.

According to the invention, an extract of *Sophora* species is provided, obtainable by:
a) one or more extractions from *Sophora* species, using a solvent selected from the group consisting of:
   i) aqueous alcohols and aqueous ketones; and
   ii) esters, including aqueous or water-saturated esters;
b) draining off the solvent from the alcoholic or ketonic solution obtained at step a)i);
c) i) one or more distributions of the residue obtained at step b) between an organic solvent selected from the group consisting of ethylacetate, tert-butylmethylether, n-butanol and butanon and water, and combining the solvent phases thus obtained; or
c) ii) one or more direct distributions of the ethylacetate extract obtained at step a)ii) with water; and
d) concentrating the combined organic solvent-phases obtained in c) till dry.

The ratio of drug to solvent at each extraction is in the range of around 1:7 to 1:10.

In a preferred embodiment, extraction at step a) is performed twice.

The solvent used at step a) should preferably be selected from the group consisting of aqueous ethanol, aqueous acetone and aqueous or water-saturated ethylacetate. In particular, the solvent used at step a) is 70% [v/v] (62% [w/w]) ethanol, 60% [w/w] ethanol or water-saturated ethylacetate.

The alcohols or ketones used at step a)i) are preferably applied as 10-96% [v/v] or [w/w], or 10-99% [v/v] or [w/w], particularly 50-92% [v/v] or [w/w] aqueous mixtures.

At step c)i), ethylacetate is the preferred solvent.

At step c) of the procedure, what takes place is essentially a thinning-out of the total alkaloid content. The extract obtainable under the invention is characterised in that it has a total alkaloid content below 0.2%, and preferably below 0.1%. In particular, the extract obtained under the invention is free of alkaloid. In this context, the term "alkaloid-free" means that it is undetectable using standard analytical procedures such as HPLC. Furthermore, the extract under the invention is characterised in containing flavones, isoflavones, chalcones and pterocarpanes. Flavone compounds can be isoprenylated, such as prenyl derivatives of naringenine. Isoflavone compounds may, if necessary, be mono-, bi- or tri-hydroxy substituted or 0-methylated. In addition, the extract may contain glycosidated flavone and isoflavone compounds. In particular, the extract according to the invention contains maackiain, maackiain glucoside, 8-prenylnaringenine, kushenol X, 8prenylkaempferol, leachianon G, kushenol E and 2,4,4',6' tetra-hydroxy 3'lavandulyl 2' methoxychalcone.

The extract can be produced from one of the family of *Sophora* species comprising *Sophora flavescens, Sophora subprostrata, Sophora alopeculoides, Sophora japonica,*

*Sophora tonkinensis, Sophora tomentosa, Sophora moorcroftiana* and *Sophora leachiana*; preferably *Sophora flavescens* or *Sophora subprostrata*.

The extracts obtainable according to the invention can be processed together with conventional pharmaceutically-acceptable additives to pharmaceutical preparations such as capsules, film tablets or coated tablets, wherein as conventional pharmaceutically-acceptable additives fillings, bonding agents, spreaders, lubricants and coatings for film and coated tablets, as well as oils or fats as excipients for capsules, can be used.

The extracts obtainable under the invention can be used for the prophylaxis and treatment of pathological conditions caused by oestrogen deficiency or by dysregulations of sex hormone metabolism, in particular oestrogen metabolism.

The pathological conditions can be selected from those belonging to the group consisting of climacteric complaints, sex hormone-dependent cancers, benign prostate hyperplasia, osteoporosis, Alzheimer's disease and cardiovascular diseases: the cancers included here comprise breast cancer, prostate cancer and cancer of the womb.

The extracts according to the invention are applied to humans at a dosage from 1-1000 mg daily, preferably 100-1000 mg daily.

A treatment is made available by using the combination according to the invention that comprises flavones, isoflavones, chalcones, pterocarpanes and other similar compounds that is particularly suitable for combating pathological conditions caused by oestrogen deficiency or by dysregulations of sex hormone metabolism, in particular oestrogen metabolism.

The following examples describe the invention and should not be considered to limit the invention. All percentage details refer to the weight, unless specified otherwise.

EXAMPLE 1

Production of an Extract From *Sophora flavescens* a) Extraction 2 kg of ground *Sophora flavescens* roots were mixed with 14 kg 70% [v/v] (62% [w/w]) ethanol, extracted by spinning (Ultraturrax) for 5 min and then stirred intensively for 1 hr at 50° C. Then it was filtered with suction over a Supra Seitz 1500 filter and the drug residue was then extracted for a second time in the same way. Both the extract solutions were combined and the dry extract content was determined using an aliquot. It turned out that there was a dry residue of 475.6 g, corresponding to a yield of 23.8%.

b) Distribution

The ethanol was removed from the extract solution on the rotary evaporator at 50° C. The watery residue (5 l) was stirred three times with 2 l ethylacetate each time, the ethylacetate phases were combined and concentrated in the rotary evaporator till dry.

Ethylacetate extract = 67.84 g (3.4% by reference to the drug;

14.3% by reference to total extract).

According to the HPLC analysis, the ethylacetate extract contains flavones, isoflavones, chalcones, pterocarpanes (e.g. 8-prenylnaringenine, daidzein, kushenol X, norkurarinon, maackiain, genistein, prenylkaempferol). There was no evidence of alkaloids.

This combination of substances is preferably suited to the prophylaxis and treatment of pathological conditions caused by oestrogen deficiency or by dysregulations of sex hormone metabolism, in particular oestrogen metabolism (compare example 5).

EXAMPLE 2

Production of an Extract From *Sophora subprostrata* a) Extraction 1 kg of ground *S. subprostrata* roots was mixed with 7 kg 70% [v/v] (62% [w/w]) ethanol, extracted by spinning (Ultraturrax) for 5 minutes and then stirred intensively at 50° C. for 1 hour. Then it was filtered with suction over a Supra Seitz 1500 filter and the drug residue was then extracted for a second time in the same way. Both the extract solutions were combined and the dry extract content was determined using an aliquot. It turned out that there was a dry residue of 111.8 g, corresponding to a yield of 11.2%.

b) Distribution

The ethanol was removed from the extract solution on the rotary evaporator at 50° C. The watery residue (2.5 l) was stirred thrice with 1 l ethylacetate each time, the ethylacetate phases were combined and concentrated in the rotary evaporator till dry.

Ethylacetate extract = 10.4 g (1.0% by reference to the drug; 9.3% by reference to total extract)

EXAMPLE 3

36 kg of ground *Sophora flavescens* drug was mixed with 7.7 times its weight made up of 60% (w/w) ethanol. Given vigorous stirring and with Dispax (Ultraturrax) in circulation, the extract solution was extracted for 1 hr at 50° C. The extract solution was filtered clear, the drug residue was once again extracted with 7 times its weight made up of 60% (w/w) ethanol under the same conditions, and finally filtered.

The extract solution was then concentrated in the centrifugal evaporator to an ethanol content of 3.5% and dry extract content of 10.52%. This concentrated solution was then distributed against water-saturated ethylacetate three times at a 1:0.4 ratio by volume. The ethylacetate phase was concentrated at the rotary evaporator and dried out in the drying cupboard at 60° C.

This resulted in:

Ethylacetate extract: 1.188 kg after grinding (3.3% by reference to the drug).

HPLC content of pharmacologically relevant substances:

| | |
|---|---|
| Maackiain glucoside | 2.8% |
| 8-prenylnaringenine | 0.4% |
| Maackiain | 0.6% |
| Kushenol X | 1.3% |
| 8-prenylkaempferol | 0.7% |

-continued

| | |
|---|---|
| Leachianon G | 6.6% |
| Kushenol E | 0.3% |
| 2,4,4',6'-tetrahydroxy-3'-lavandulyl-2'-methoxychalcone | 0.7% |

There was also evidence of daidzein and genistein. There was no evidence of any alkaloids.

Estrogenic activity could be shown for each of the substances mentioned in a yeast assay according to example 5. The oestrogenic activity for the extract is produced by the Reportergen assay with the use of yeast cells according to example 5: compare FIG. 3.

HPLC Method

| | |
|---|---|
| Columns | LiChrospher 100 5 µm, 250 × 4 mm |
| Eluens | A: 1000 ml bidest water/3 ml phosphoric acid (85%)/2 ml triethylamine<br>B: 100 ml acetonitril/3 ml phosphoric acid (85%)/2 ml triethylamine/60 ml bidest water |

| Gradient | % A | | % B |
|---|---|---|---|
| | 0 min 70 | | 30 |
| | 30 min 30 | | 70 |
| | 35 min 0 | | 100 |
| Flow | 1.2 ml/min | | |
| Detection | 220 nm | | |

EXAMPLE 4

150 g of ground *Sophora flavescens* drug was extracted twice with water-saturated ethylacetate at the ratio of 1:7 (m/m). Therefore, the drug was broken down beforehand with an Ultra-Turrax for five minutes (extraction by movement). The drug was then extracted under reflux for 1 hour at 60° C. The combined extract solutions were then filtered off and the ethylacetate extract solution thus obtained was shaken back twice with ethylacetate-saturated water at the ratio 1:1 [v/v]. The combined ethylacatate phases were concentrated till dry.

Yield: 3.99% by reference to the drug.

EXAMPLE 5

Testing the ethylacetate extracts produced for oestrogenic activity with transfected yeast cells, which express the human α oestrogen receptor.

The testing of extracts for oestrogenic properties was performed with a Reportergen assay, using yeast cells (saccharomyces). These cells are stable with the human α oestrogen receptor and an expression plasmid which contains an oestrogen response element and the gene for the enzyme β galactosidase. All samples were dissolved in DMSO at a concentration of 20 mg/ml, and were given undiluted or after diluting with DMSO at the ratio of 1/10, 1/100 or at a volume of 1 µl to 100 µl culture medium in 96-well flat-bottom micro-titre dishes. Next, 100 µl yeast suspension and the chromogenous substrate chlorophenol-red-β-D-galactopyranoside were added. Control wells were provided on every dish, which were filled with either the culture medium or the solvent alone, or which contained the standard concentrations of 17 β oestradiol. The yeast cells were incubated for 72 hours at 32° C., after which absorption of the medium was measured at 540 nm in a micro-titre dish photometer. The samples were sometimes checked twice.

Results:

Sample Concentrations:

| Dilution | Concentration |
|---|---|
| undiluted | 100 µg/ml |
| 1:10 | 10 µg/ml |
| 1:100 | 1 µg/ml |

Designation of Samples:

| Sample number | Sample | Number of tests | *Sophora* species |
|---|---|---|---|
| A | 70% [v/v] (62% [w/w]) ethanol extract according to ex. 1a) | 1 | *Sophora flavescens* |
| B | 70% [v/v] (62% [w/w] (ethanol extract according to ex. 2a) | 1 | *Sophora subprostrata* |
| C | 70% [v/v] (62% [w/w]) ethanol extract according to ex. 1a) | 2 | *Sophora flavescens* |
| D | Ethylacetate extract according to ex. 1b) | 1 | *Sophora flavescens* |
| E | Ethylacetate extract according to ex. 2b) | 1 | *Sophora subprostrata* |
| F | Ethylacetate extract according to ex. 3 | 1 | *Sophora flavescens* |

Figure 2:
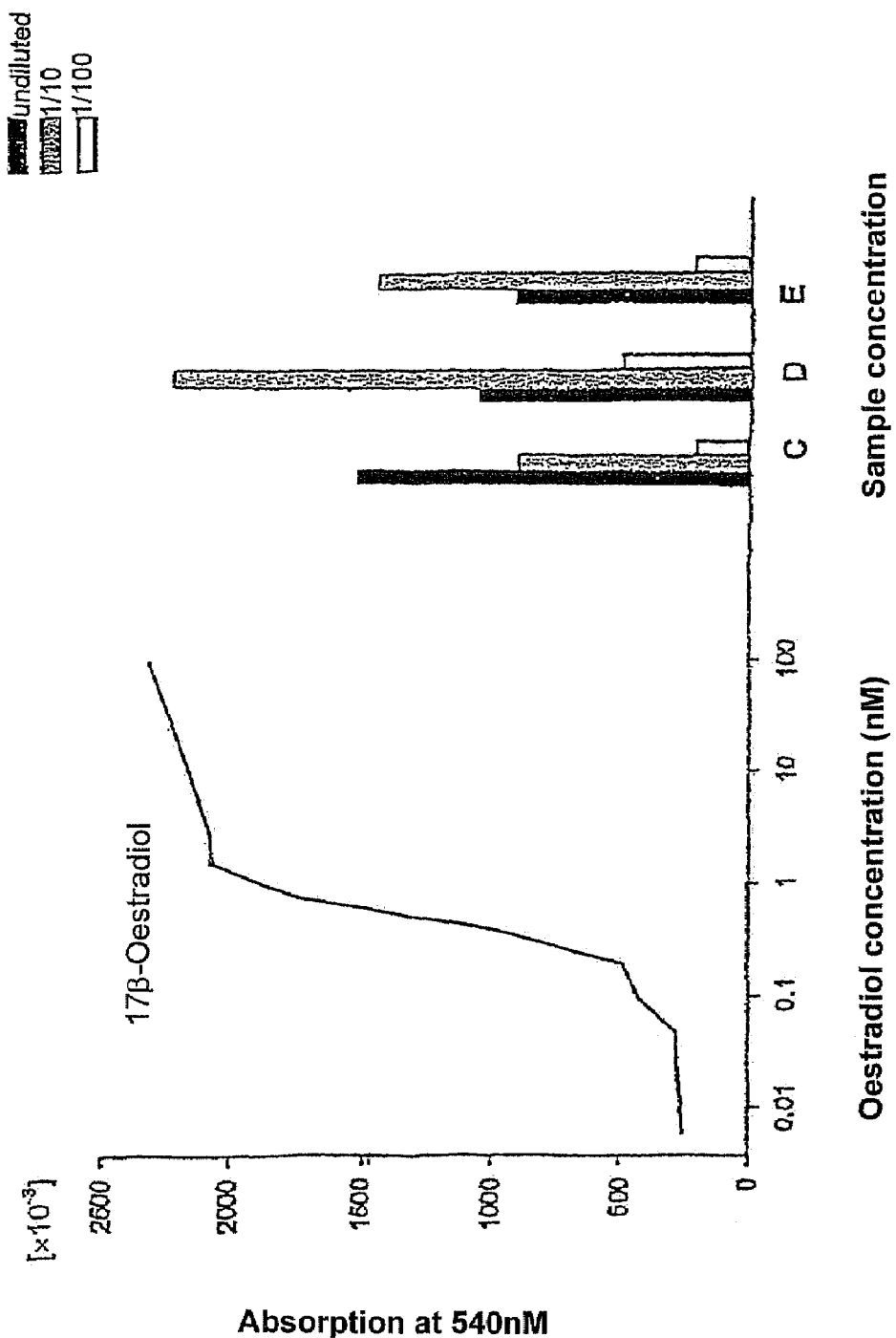
FIG. 2 illustrates the oestrogenic activity of extracts according to the invention (70% [v/v] or 62% [w/w] ethanol extracts after distribution with ethylacetate; according to examples 1b) and 2b)) from *Sophora flavescens* and *Sophora subprostrata* in a yeast assay, compared with 17β oestradiol.
Figure 3:
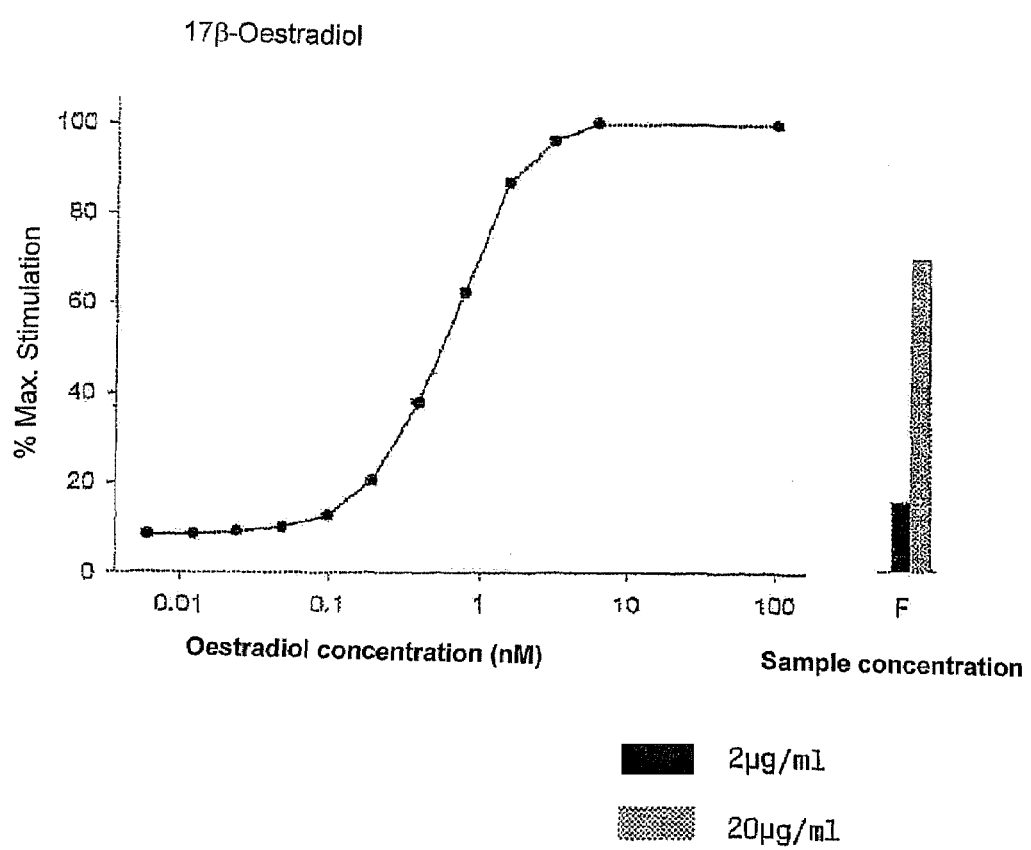
FIG. 3 illustrates the oestrogenic activity of extracts according to the invention (60% [w/w] ethanol extracts after distribution with ethylacetate according to example 3) from *Sophora flavescens* in a yeast assay, compared with 17β oestradiol.

The results of the assays are depicted in FIGS. 1, 2 and 3. In so doing, the oestrogenic activity of the extracts was compared against the activity of 17β oestradiol. For this purpose, extracts that can be designated as "active" are those whose activity when compared with 17β oestradiol matches the activity of 17β oestradiol that has become established within the distinctly rising segment of the 17β oestradiol activity curve (and hence from a concentration of around 0.1-0.2 nM of 17β oestradiol).

In particular, FIG. 1 illustrates the oestrogenic activity of 70% [v/v] (62% [w/w]) ethanol extracts (according to examples 1a) and 2a)) from *Sophora flavescens* and *Sophora subprostrata* in a yeast assay, compared with 17β oestradiol.

FIG. 2 illustrates the oestrogenic activity of the extracts under this invention (70% [v/v] or 62% [w/w] ethanol extract after distribution with ethylacetate; according to examples 1b) and 2b)) from *Sophora flavescens* and *Sophora subprostrata* in a yeast assay, compared with 17 β oestradiol.

FIG. 3 illustrates the oestrogenic activity of extracts according to the invention (60% [w/w] ethanol extracts after distribution with ethylacetate according to example 3) from *Sophora flavescens* in a yeast assay, compared with 17β oestradiol.

The invention claimed is:

1. An extract of *Sophora flavescens* or *Sophora subprostrata* root comprising a total alkaloid content below 0.2%.

2. The extract according to claim 1, comprising a total alkaloid content below 0.1%.

3. The extract according to claim 1, wherein the extract is free of alkaloids.

4. A pharmaceutical composition comprising the extract of claim 1 and a pharmaceutically acceptable carrier.

* * * * *